United States Patent
Puskarich (10) Patent No.: US 11,954,249 B1
(45) Date of Patent: Apr. 9, 2024

(54) HEAD-MOUNTED SYSTEMS WITH SENSOR FOR EYE MONITORING

(71) Applicant: Apple Inc., Cupertino, CA (US)

(72) Inventor: Paul G. Puskarich, London (GB)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/328,718

(22) Filed: May 24, 2021

Related U.S. Application Data (60) Provisional application No. 63/044,778, filed on Jun. 26, 2020.

(51) Int. Cl.
| | |
|---|---|
| *G06F 3/01* | (2006.01) |
| *A61B 5/00* | (2006.01) |
| *A61B 5/398* | (2021.01) |
| *G02B 27/01* | (2006.01) |
| *G06F 3/16* | (2006.01) |

(Continued)

(52) U.S. Cl.
CPC .............. *G06F 3/013* (2013.01); *A61B 5/398* (2021.01); *A61B 5/4812* (2013.01); *A61B 5/6803* (2013.01); *G02B 27/0172* (2013.01); *G02B 27/0179* (2013.01); *G06F 3/012* (2013.01); *G06F 3/16* (2013.01); *G01S 19/13* (2013.01);

(Continued)

(58) Field of Classification Search
CPC ...... G02B 2027/0138; G02B 2027/014; G02B 2027/0141; G02B 2027/0178; G02B 2027/0187; G02B 27/017; G02B 27/0172; G02B 27/0179; G06F 1/163; G06F 1/1686; G06F 1/1688; G06F 3/011; G06F 3/013; G06F 3/017; G06F 3/0304; G06F 3/16; G06F 40/58; G06T 19/006; G06T 2207/20084; G06T 7/70; G06V 10/10; G06V 20/20; G06V 30/10; G06V 40/28; G06V 10/82; G06V 20/41; G06V 20/46; G06V 40/15; G06V 40/161; G06V 40/169; G06V 40/40; G06V 40/45
See application file for complete search history.

(56) References Cited

U.S. PATENT DOCUMENTS

| | | | | |
|---|---|---|---|---|
| 5,726,916 A | * | 3/1998 | Smyth | A61B 5/398 351/210 |
| 6,204,974 B1 | * | 3/2001 | Spitzer | G02C 11/10 359/633 |

(Continued)

*Primary Examiner* — Ram A Mistry (74) *Attorney, Agent, or Firm* — Treyz Law Group, P.C.; G. Victor Treyz; Tianyi He (57) ABSTRACT

A head-mounted device may have a head-mounted housing. The head-mounted housing may have displays that overlap a user's eyes and/or speakers that provide sound to the user's ears. The head-mounted housing may have transparent lenses that overlap the eyes of the user or may have opaque structures that prevent ambient light from reaching the user's eyes. The head-mounted device may have a geographic location sensor such as a satellite navigation system sensor and may include an orientation sensor such as an inertial measurement unit. The direction of a user's gaze relative to the head mounted device may be measured using an electrooculographic sensor. Electrodes in the electrooculographic sensor may measure signals resulting from the standing potential between the retina and cornea in the eye. Facial expressions and eye blinks may affect the signals detected with the electrodes and can be monitored during operation.

16 Claims, 9 Drawing Sheets

(51) Int. Cl.
*G01S 19/13* (2010.01)
*G06F 3/04842* (2022.01)

(52) U.S. Cl.
CPC ............... *G02B 2027/0141* (2013.01); *G02B 2027/0187* (2013.01); *G06F 3/04842* (2013.01)

(56) References Cited

U.S. PATENT DOCUMENTS

| | | | |
|---|---|---|---|
| 8,333,475 | B2 | 12/2012 | Sugio et al. |
| 9,451,068 | B2 | 9/2016 | Warren |
| 9,486,156 | B2 | 11/2016 | Kato et al. |
| 9,619,021 | B2 | 4/2017 | Cho et al. |
| 9,691,241 | B1 | 6/2017 | Braun et al. |
| 10,073,518 | B2 | 9/2018 | Rahman et al. |
| 10,299,674 | B2 | 5/2019 | Correns et al. |
| 2016/0057565 | A1* | 2/2016 | Gold ..................... H04W 4/023 455/41.1 |
| 2016/0080874 | A1* | 3/2016 | Fullam ................... G06F 3/013 381/313 |
| 2017/0115742 | A1* | 4/2017 | Xing ..................... G06F 3/0485 |
| 2017/0337742 | A1* | 11/2017 | Powderly ......... G06K 19/06009 |
| 2018/0184002 | A1* | 6/2018 | Thukral ................ G06F 3/0304 |
| 2019/0285881 | A1* | 9/2019 | Llic ........................ G06F 3/013 |

\* cited by examiner

HEAD-MOUNTED SYSTEMS WITH SENSOR FOR EYE MONITORING

This application claims the benefit of provisional patent application No. 63/044,778, filed Jun. 26, 2020, which is hereby incorporated by reference herein in its entirety.

FIELD

This relates generally to electronic devices, and, more particularly, to electronic devices such as head-mounted devices.

BACKGROUND

Electronic devices such as head-mounted devices may have displays for displaying images. The displays may be housed in a head-mounted support structure.

SUMMARY

A head-mounted device may have a head-mounted housing that is worn on the head of a user. The head-mounted housing may have displays that overlap a user's eyes or may not contain displays. Speakers may be provided in the housing to provide audio output to the user's ears.

The head-mounted housing may have transparent lenses that overlap the eyes of the user or may have opaque structures that prevent ambient light from reaching the user's eyes. Opaque structures may, for example, be used in a head-mounted device such as a sleep mask or pair of meditation glasses that block ambient light. Opaque structures covering the user's eyes may also be used in head-mounted devices such as virtual reality goggles that have forward-facing cameras that capture images of the real world.

Head-mounted devices with clear lenses that overlap the user's eyes may include optical combiners in these lenses for merging computer-generated content with real-world images. In some arrangements, head-mounted devices without displays may have clear lenses that allow the user to view the surrounding environment.

A head-mounted device may have a geographic location sensor such as a satellite navigation system sensor and may include an orientation sensor such as an inertial measurement unit. The direction of a user's gaze relative to the head mounted device may be measured using an electrooculographic sensor and, if desired, optional image-sensor-based gaze tracking systems. By using geographic location information, orientation information, and gaze information, and by using pattern recognition techniques and/or on-line database look-up techniques, the head-mounted device may identify objects in the user's environment and can identify which of these objects is currently being viewed by the user. Action can then be taken based on the identified currently-viewed object. For example, a visual label may be presented for the object, an audible output related to the object may be presented, selectable options (visible, audible, etc.) that are associated with the object may be presented, etc.

Electrodes in an electrooculographic sensor may measure signals resulting from the standing potential between the retina and cornea in the eye. These signals may be processed to determine the direction of a user's gaze without using an image-sensor-based gaze tracking system. Facial expressions and eye blinks can impact the signals detected with the electrodes and can therefore be monitored during operation of the electrooculographic sensor. Information on facial expressions, eye blinks, and gaze can be used to animate an avatar or may be used in presenting other computer-generated content.

A head-mounted device with an image-sensor-based gaze tracking system and an electrooculographic sensor may use different sensors in different operating modes. For example, a gaze tracking system based on an image sensor may, in a given mode of operation, be used to gather gaze information to supplement and/or replace eye orientation information from an electrooculogram. In another mode of operation, the electrooculographic sensor may be used to track eye motion without using the image-sensor-based gaze tracking system.

DETAILED DESCRIPTION

Head-mounted devices include head-mounted support structures that allow the devices to be worn on the heads of users. Head-mounted devices may include input-output devices for gathering input and supplying a user with output. For example, head-mounted devices may include speakers for presenting a user with audio output and/or may include displays for presenting a user with visual content.

During use of a head-mounted device, it may be desirable to monitor eye movements. For example, eye movements may provide information about whether the user is awake or asleep. Eye movement data may also supply information about the direction of a user's gaze. Information on the user's gaze (direction of viewing) may be used as input to the device, may be used to help efficiently display foveated content on a display, may be used to determine which virtual and/or real objects in the user's field of view are currently being viewed by the user to provide the device with context (e.g., so that a user may request more information about the currently viewed object, so that the device can automatically supply such information, etc.), and/or may otherwise be used by the head-mounted device.

A head-mounted device may include one or more gaze tracking systems such as systems based on image sensors that detect and process eye glints (eye reflections arising when the eye is illuminated by light-emitting diodes or other light-sources near the eye) and/or that detect and process images of the user's eye (e.g., retinal images, images of the user's pupil, etc.). Gaze tracking systems such as these may operate at infrared and/or visible wavelengths.

To supplement these devices and/or to help reduce bulk, complexity, and/or weight, eye monitoring can also be performed by gathering electrical measurements of the user's skin near the user's eyes. These measurements are sometimes referred to as electrooculograms. The human eye exhibits a standing potential between the cornea and retina. Electooculographic measurements made from eye monitoring electrodes near a user's eye can be used to detect the user's eye motions and direction of gaze. In some configurations, electrooculograms can be influenced by eye blinks and movement of facial muscles, so electrooculograms may also reveal information on a user's eye blinks and facial expressions.

Figure 1:
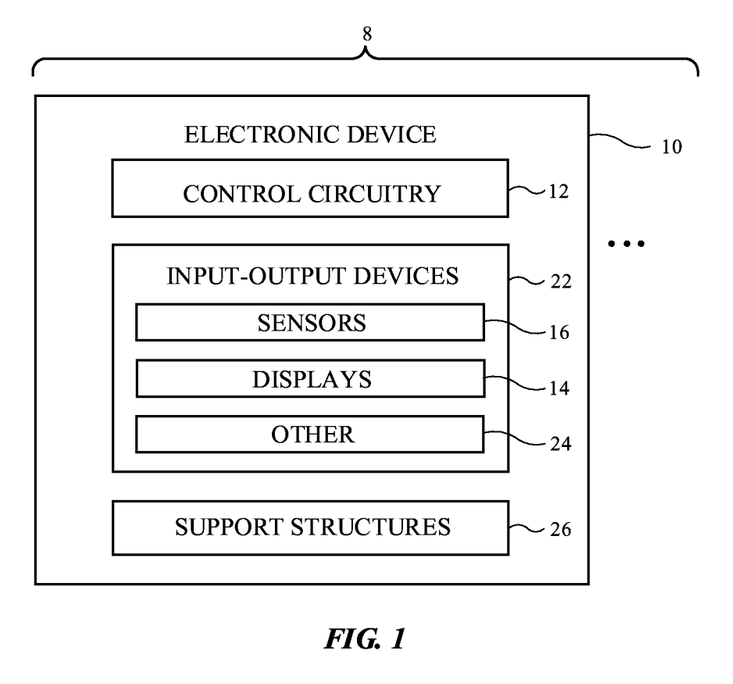
FIG. 1 is a schematic diagram of an illustrative electronic device such as a head-mounted display device in accordance with an embodiment.

A schematic diagram of an illustrative system that may include a head-mounted device that gathers electrooculographic measurements is shown in FIG. 1. As shown in FIG. 1, system 8 may include one or more electronic devices such as electronic device 10. The electronic devices of system 8 may include computers, cellular telephones, head-mounted devices, wristwatch devices, and other electronic devices. Configurations in which electronic device 10 is a head-mounted device are sometimes described herein as an example. Head-mounted devices may include goggles, helmets, glasses, sleep masks, and/or other equipment that may be worn over a user's eyes.

As shown in FIG. 1, electronic devices such as electronic device 10 may have control circuitry 12. Control circuitry 12 may include storage and processing circuitry for controlling the operation of device 10. Circuitry 12 may include storage such as hard disk drive storage, nonvolatile memory (e.g., electrically-programmable-read-only memory configured to form a solid-state drive), volatile memory (e.g., static or dynamic random-access-memory), etc. Processing circuitry in control circuitry 12 may be based on one or more microprocessors, microcontrollers, digital signal processors, baseband processors, power management units, audio chips, graphics processing units, application specific integrated circuits, and other integrated circuits. Software code may be stored on storage in circuitry 12 and run on processing circuitry in circuitry 12 to implement control operations for device 10 (e.g., data gathering operations, operations involving the adjustment of the components of device 10 using control signals, etc.). Control circuitry 12 may include wired and wireless communications circuitry. For example, control circuitry 12 may include radio-frequency transceiver circuitry such as cellular telephone transceiver circuitry, wireless local area network transceiver circuitry (e.g., WiFi® circuitry), millimeter wave transceiver circuitry, and/or other wireless communications circuitry.

During operation, the communications circuitry of the devices in system 8 (e.g., the communications circuitry of control circuitry 12 of device 10), may be used to support communication between the electronic devices. For example, one electronic device may transmit video data, audio data, and/or other data to another electronic device in system 8. Electronic devices in system 8 may use wired and/or wireless communications circuitry to communicate through one or more communications networks (e.g., the internet, local area networks, etc.). The communications circuitry may be used to allow data to be received by device 10 from external equipment (e.g., a tethered computer, a portable device such as a handheld device or laptop computer, online computing equipment such as a remote server or other remote computing equipment, or other electrical equipment) and/or to provide data to external equipment.

Device 10 may include input-output devices 22. Input-output devices 22 may be used to allow a user to provide device 10 with user input. Input-output devices 22 may also be used to gather information on the environment in which device 10 is operating. Output components in devices 22 may allow device 10 to provide a user with output and may be used to communicate with external electrical equipment.

As shown in FIG. 1, input-output devices 22 may include one or more optional displays such as displays 14. In some configurations, device 10 includes left and right display devices. Device 10 may, for example, include left and right components such as left and right scanning mirror display devices or other image projectors, liquid-crystal-on-silicon display devices, digital mirror devices, or other reflective display devices, left and right display panels based on light-emitting diode pixel arrays (e.g., organic light-emitting display panels or display devices based on pixel arrays formed from crystalline semiconductor light-emitting diode dies), liquid crystal display panels, and/or or other left and right display devices that provide images to left and right eye boxes for viewing by the user's left and right eyes, respectively.

Displays 14 may be used to display visual content for a user of device 10. The content that is presented on displays 14 may include virtual objects and other content that is provided to displays 14 by control circuitry 12. This virtual content may sometimes be referred to as computer-generated content. Computer-generated content may be displayed in the absence of real-world content or may be combined with real-world content. In some configurations, a real-world image may be captured by a camera (e.g., a forward-facing camera, sometimes referred to as a front-facing camera) so that computer-generated content may be electronically overlaid on portions of the real-world image (e.g., when device 10 is a pair of virtual reality goggles with an opaque display). In other configurations, an optical coupling system may be used to allow computer-generated content to be optically overlaid on top of a real-world image. As an example, device 10 may have a see-through display system that provides a computer-generated image to a user through a beam splitter, prism, holographic coupler, or other optical coupler while allowing the user to view real-world objects through the optical coupler.

Input-output circuitry 22 may include sensors 16. Sensors 16 may include, for example, three-dimensional sensors (e.g., three-dimensional image sensors such as structured light sensors that emit beams of light and that use two-dimensional digital image sensors to gather image data for three-dimensional images from light spots that are produced when a target is illuminated by the beams of light, binocular three-dimensional image sensors that gather three-dimensional images using two or more cameras in a binocular imaging arrangement, three-dimensional lidar (light detection and ranging) sensors, three-dimensional radio-frequency sensors, or other sensors that gather three-dimensional image data), cameras (e.g., infrared and/or visible digital image sensors), gaze tracking sensors (e.g., a gaze tracking system based on an image sensor and, if desired, a light source that emits one or more beams of light that are tracked using the image sensor after reflecting from a user's eyes), touch sensors, capacitive proximity sensors, light-based (optical) proximity sensors, other proximity sensors, force sensors, sensors such as contact sensors based on switches, gas sensors, pressure sensors, moisture sensors, magnetic sensors, audio sensors (microphones), ambient light sensors, microphones for gathering voice commands and other audio input, sensors that are configured to gather information on motion, position, and/or orientation (e.g., accelerometers, gyroscopes, compasses, and/or inertial measurement units that include all of these sensors or a subset of one or two of these sensors), and/or other sensors. To monitor eye movements, sensors 16 may include one or more electrooculography sensors. Electrooculography sensors have eye monitoring electrodes that gather voltage measurements near to a user's eye. These signal measurements may be processed using electrooculography processing circuitry (e.g., control circuitry 12) to produce eye movement information and, if desired, gaze tracking information (e.g., information on a user's direction of gaze).

User input and other information may be gathered using sensors and other input devices in input-output devices 22. If desired, input-output devices 22 may include other devices 24 such as haptic output devices (e.g., vibrating components), light-emitting diodes and other light sources, speakers such as ear speakers for producing audio output, circuits for receiving wireless power, circuits for transmitting power wirelessly to other devices, batteries and other energy storage devices (e.g., capacitors), joysticks, buttons, and/or other components.

Electronic device 10 may have housing structures (e.g., housing walls, straps, etc.), as shown by illustrative support structure 26 of FIG. 1. In configurations in which electronic device 10 is a head-mounted device (e.g., a pair of glasses, goggles, a helmet, a hat, a sleep mask, etc.), support structure 26 may include head-mounted support structures (e.g., a helmet housing, head straps, temples in a pair of eyeglasses, goggle housing structures, a mask covering layer, and/or other head-mounted structures). The head-mounted support structures may be configured to be worn on a head of a user (e.g., over the user's eyes) during operation of device 10 and may support displays 14, sensors 16, other components 24, other input-output devices 22, and control circuitry 12.

Figure 2:
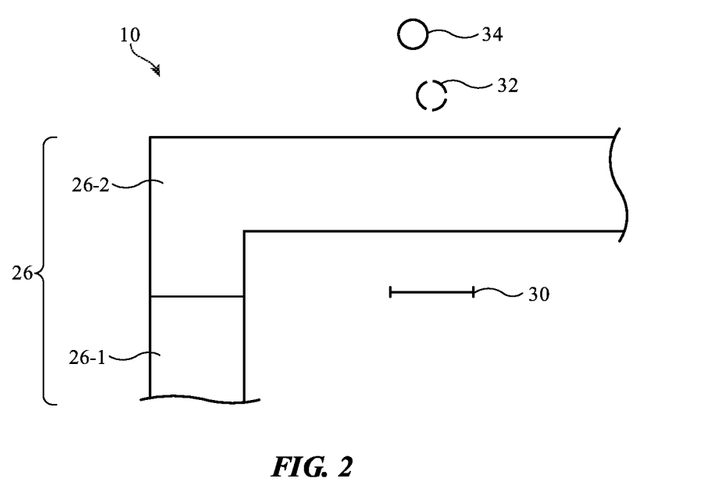
FIG. 2 is a top view of an illustrative head-mounted device in accordance with an embodiment.

FIG. 2 is a top view of a portion of electronic device 10 in an illustrative configuration in which electronic device 10 is a head-mounted device. As shown in FIG. 2, electronic device 10 may include head-mounted support structure 26 to house the components of device 10 and to support device 10 on a user's head. Support structure 26 may include, for example, structures that form housing walls and other structures at the front of device 10 (e.g., support structures 26-2, which may form frame structures such as a nose bridge, end pieces, and/or other housing structures) and additional structures such as straps, temples, or other supplemental support structures (e.g., support structures 26-1) that help to hold the main unit and the components in the main unit on a user's face so that the user's eyes are located within eye boxes (eye locations) such as eye box 30.

During operation of device 10, images may be presented to a user's eyes in eye boxes 30. Eye boxes 30 include a left eye box (e.g., eye box 30 of FIG. 2) that receives a left image and a right eye box that receives a right image. Device 10 may include a left display system with a left display 14 that presents the left image to the left eye box and a right display system with a right display 14 that presents the right image to the right eye box. In an illustrative configuration, each display system may have an optical combiner assembly that helps combine display images (e.g., computer-generated image 32 of FIG. 2, sometimes referred to as a virtual image) with real-world image light (e.g., light from real-world objects such as object 34 of FIG. 2). Optical combiner assemblies may include optical couplers, waveguides, and/or other components.

In some configurations, device 10 may contain no optical combiner assemblies.

In a first illustrative example in which device 10 does not contain optical combiner assemblies, device 10 may be a pair of virtual reality goggles or other device that has an opaque front face covering eye boxes 30 (e.g., structures 26-2 may be opaque structures that overlap and cover a user's eyes, thereby blocking ambient light). The goggles may use forward-facing cameras to capture images of real-world objects and may present corresponding images on displays 14. These images may include real-world content captured by the forward-facing cameras and may include computer-generated content that has been digitally combined with the real-world content.

In a second illustrative example in which device 10 does not contain optical combiner assemblies, device 10 may be pair of meditation glasses or a sleep mask that has an opaque front portion but that does not have forward-facing cameras. In this type of arrangement, displays 14 may be used to display computer-generated content or other content for the user without displaying forward-facing camera images. If desired, displays 14 may be omitted from this type of device.

In a third illustrative example in which device 10 does not contain optical combiner assemblies, device 10 may be a pair of sunglasses or other glasses without displays 14. In this type of device, device 10 does not present images to eye boxes 30. Rather, the user may view the real world through clear lenses at the front of device 10 (e.g., lenses in support structures 26-2 that overlap eye boxes 30).

Figure 3:
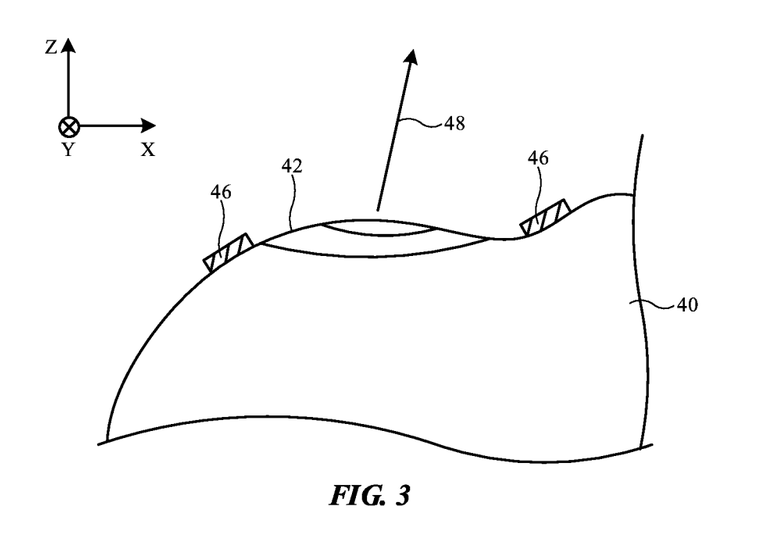
FIG. 3 is a top view of a portion of a user's head including the user's left eye and illustrative head-mounted device eye monitoring electrodes placed against the skin of the user's face adjacent to the user's left eye in accordance with an embodiment.

FIG. 3 is a top view of a portion of a user's face showing how device 10 may make electrooculography measurements. In the diagram of FIG. 3, user 40 is facing in the +Z direction. The user's eyes such as left eye 42 are gazing in direction 48 (which is off axis with respect to the +Z direction in this example). Electrodes 46 are placed adjacent to eye 42 (e.g., directly on the skin of the user's face adjacent to eye 42 or at a location adjacent to eye 42 that is sufficiently close to the user's skin to allow electrodes 46 to capacitively couple to the user's skin). When placed adjacent to the location of eye 42 in this way, electrodes 46 and associated processing circuitry in device 10 (see, e.g., control circuitry 12) form an electrooculography sensor that measures eye movements.

Figure 4:
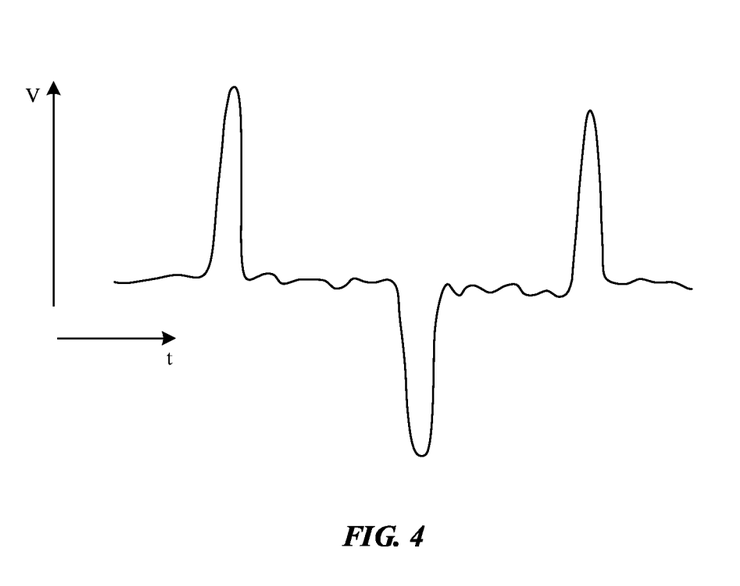
FIG. 4 is an illustrative eye monitoring signal trace gathered using eye monitoring electrodes in an electrooculographic sensor in accordance with an embodiment.

Electrodes 46, which may sometimes be referred to as eye monitoring electrodes or electrooculography electrodes, are used to measure voltages on the user's skin near eye 42 that are created by the standing potential between the retina and cornea of eye 42. These voltages vary as eye 42 is oriented in different directions and can therefore be used in measuring the angular orientation of eye 42 (e.g., the orientation of the user's gaze 48 relative to the XYZ coordinates of FIG. 3) and/or can be used in measuring eye movement (information on directional changes in gaze 48 and/or the speed of these changes). Eye blinks and movements of facial muscles may also be detected in electrooculograms. A graph of typical electrooculography measurements (measured voltage V from electrodes 46 of FIG. 3) as eye moves (and the direction of gaze 48 changes) over time is shown in FIG. 4. When eye 42 points towards a given electrode, the standing potential of the eye will cause the voltage of that electrode to rise, whereas when eye 42 points way from the given electrode, the standing potential of the eye will case the voltage of that electrode to fall. By monitoring the changes in the electrooculography electrode signals, control circuitry 12 can determine the direction in which eye 42 is oriented (e.g., direction 48 of FIG. 3, sometimes referred to as the user's gaze). Signal variations due to other effects (e.g., eye blinks and/or facial muscle movements) can be analyzed using machine learning (e.g., to determine signal patterns corresponding to particular changes in facial expression). During operation of device 10, electrooculograms can then be processed to separate eye blink and facial expression signals from gaze information.

Device 10 may have any suitable number of electrodes 46. For example, each eye may be provided with N electrodes, where the value of N is two, at least two, at least four, at least eight, fewer than 20, 2-8, 2-12, 4-10, fewer than six, or other suitable value. Electrodes 46 may be placed around both eyes 42 of a user or only around one eye. In configurations in which each eye has only two electrodes 46, these electrodes may be placed to the left and right of each eye (e.g., on a portion of the user's nose facing the eye and on an opposing outer edge of the eye) or may be placed above and below each eye (e.g., under the eye brow and on an opposing side of the eye under the eye).

Figure 5:
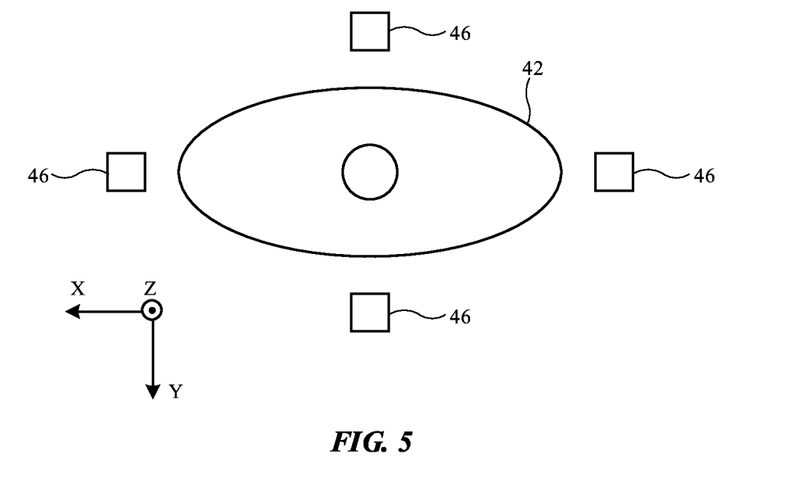
FIGS. 5 and 6 are front views of an eye showing illustrative eye monitoring electrode patterns for a head-mounted device in accordance with an embodiment.
Figure 6:
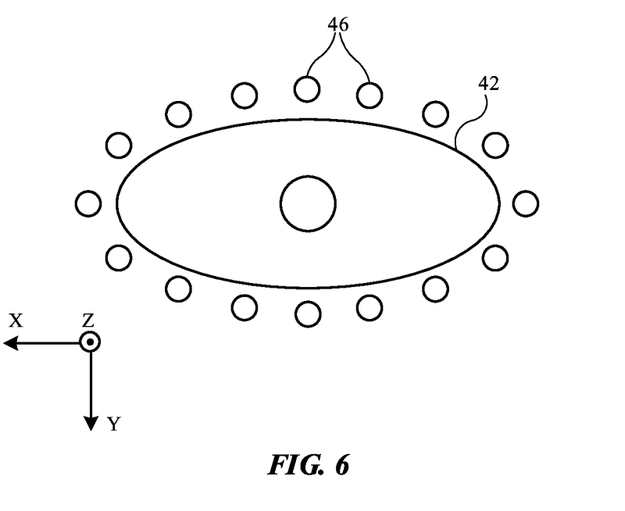

FIGS. 5 and 6 show illustrative electrode patterns that may be used for electrodes 46. Electrodes 46 may be placed on support structure 26 of device 10 so that they are positioned around locations where the user's eyes are located (e.g., facing and contacting the skin of the user's face to measure electrooculography signals). For example, electrodes 46 may be mounted on support structure 26 at positions above and below and to the left and right of eye 42, as shown in FIG. 5, or may be placed at other positions around the periphery of eye 46. If desired, one or more of electrodes 46 of FIG. 5 may be omitted. In the example of FIG. 6, there are numerous (e.g., at least ten) electrodes 46 arranged in a ring around the periphery of eye 42. Other arrangements may be used, if desired. In configurations with fewer electrodes 46, eye monitoring measurements may reveal relatively less information about eye movements but may help reduce signal processing loads and power consumption in device 10. Configurations that have more electrodes 46 can be used to gather more detailed electrooculography information and consequently more accurate details on the user's gaze, etc.

If desired, device 10 may include non-electrooculography gaze tracking sensors. For example, device 10 may include gaze tracking sensors that measure eye position using an image sensor to capture infrared eye images while the eye is illuminated by light source that creates eye reflections (glints) revealing eye gaze direction, non-electrooculography gaze tracking sensors that capture and analyze images of a user's pupil and that use pupil shape information to produce gaze tracking information, and/or non-electrooculography gaze tacking sensors that track eye gaze by capturing and analyzing retinal images (as examples). In these situations, the electrooculography sensor circuitry of device 10 can be used to help conserve power (e.g., to allow other gaze tracking sensors to be shut down until needed for enhanced accuracy) and/or may be used to gather information that supplements non-electrooculography sensor data (e.g., to gather facial expression information for portions of the user's face that are blocked from view by the image sensor in an image-sensor based system, to gather supplemental gaze information, to gather information on the user's eye movements while the user's eyes are closed, etc.).

Figure 7:
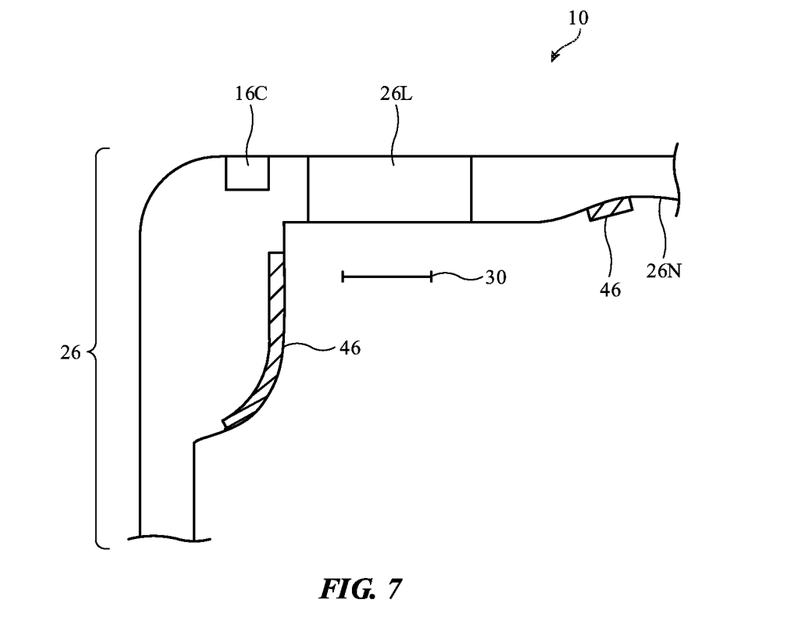
FIG. 7 is a top view of a left portion of an illustrative head-mounted device with eye monitoring electrodes in accordance with an embodiment.

FIG. 7 is a top view of a left-hand portion of an illustrative electronic device. As shown in FIG. 7, support structures 26 may be configured so that electrodes 46 are located adjacent to the locations of the user's eyes such as eye box 30. When structures 26 are worn on a user's head, electrodes 46 may press against the user's face to gather electrooculography measurements. One of electrodes 46 in the example of FIG. 7 is located on nose bridge surface 26N of a central nose-bridge portion of structures 26. The opposing outer electrode 46 on the opposing side of eye box 30 is configured to contact the user's face on the outer side of the user's eye (e.g., in front of the user's temple).

The portion of device 10 that overlaps the user's eye in eye box 30 (e.g., portion 26L) may contain a display (e.g., display 14) or an output coupler associated with a display to direct an image from the display towards eye box 30 (e.g., an output coupler that couples an image out of a waveguide that is overlapping eye box 30). If desired, portion 26L may be opaque while images from a display are provided to eye box 30 that contain both real-world content that has been captured by forward-facing cameras in structure 26 (see, e.g., camera 16C) and computer-generated content.

In some configurations, device 10 does not contain a display (e.g., no display is used to provide an image to eye box 30). In this type of arrangement, portion 26L may be transparent (e.g., portion 26L may be a transparent lens in a pair of glasses such as a pair of sunglasses) or portion 26L may be opaque (e.g., portion 26L may be formed from one or more opaque materials). In configurations such as these in which portion 26L is opaque (e.g., when device 10 is a pair of meditation glasses or a sleep mask), portions 26L may be configured to block some or all of the ambient light surrounding device 10, so that little or no ambient light reaches eye box 30.

Regardless of whether or not eye box 30 is illuminated by ambient light and/or whether a user's gaze is being tracked by an image-sensor based gaze tracking sensor, the electrooculography sensor formed with electrodes 46 may measure eye movements. For example, if a user is sleeping while wearing a sleep mask, the electrooculography sensor formed using electrodes 46 can measure the user's eye movements (e.g., to monitor a user's sleep cycles such as a non-rapid-eye-movement sleep cycle, a rapid eye movement sleep cycle, etc.). These measurements may be made even if the user's eyes are closed. Similarly, when device 10 is a pair of meditation glasses, the user's meditation state can be monitored (and, if desired, audible feedback or other feedback given) using electrooculography sensor measurements of the user's eyes, whether or not the user's eyes are closed.

Figure 8:
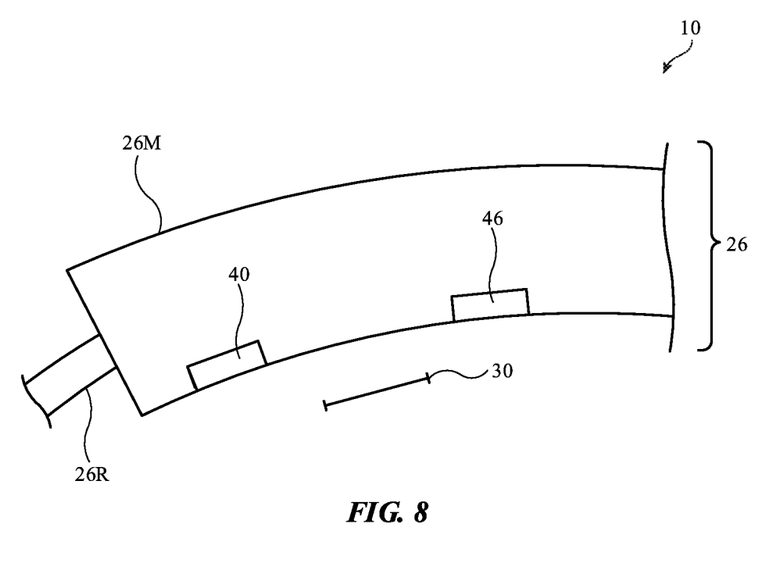
FIG. 8 is a top view of an illustrative head-mounted device with a strap and eye monitoring electrodes in accordance with an embodiment.

FIG. 8 is a top view of an illustrative left-hand portion of device 10 in an illustrative configuration in which device 10 is a sleep sensor, a pair of goggles, or other device having portions that wrap around the rear portion of a user's head (e.g., head strap portion 26R). Support structure 26 of device 10 in FIG. 8 has a main portion (portion 26M) that overlaps and covers eye boxes 30. Portion 26M, which may be opaque to block ambient light, may some or all of the front of the user's face and may therefore be formed from soft comfortable materials such as soft fabric, foam, air-filled bladders, etc. This type of support structure may support electrodes 46 so that they contact the skin of the user adjacent to the user's eye when the user's eye is located in eye box 30. In some configurations, an internal frame may be formed for this type of device (e.g., a rigid chassis and other support structures formed from metal, rigid polymer, glass, etc.). The components of FIG. 1 may be supported by these frame structures. Some or all of the frame may be covered with cosmetic covering layers such as layers of fabric, and/or other housing structures (e.g., to form a pair of goggles that is held to a user's face with head strap 26R, to form a sleep mask made partly or primarily of fabric, etc.).

Figure 9:
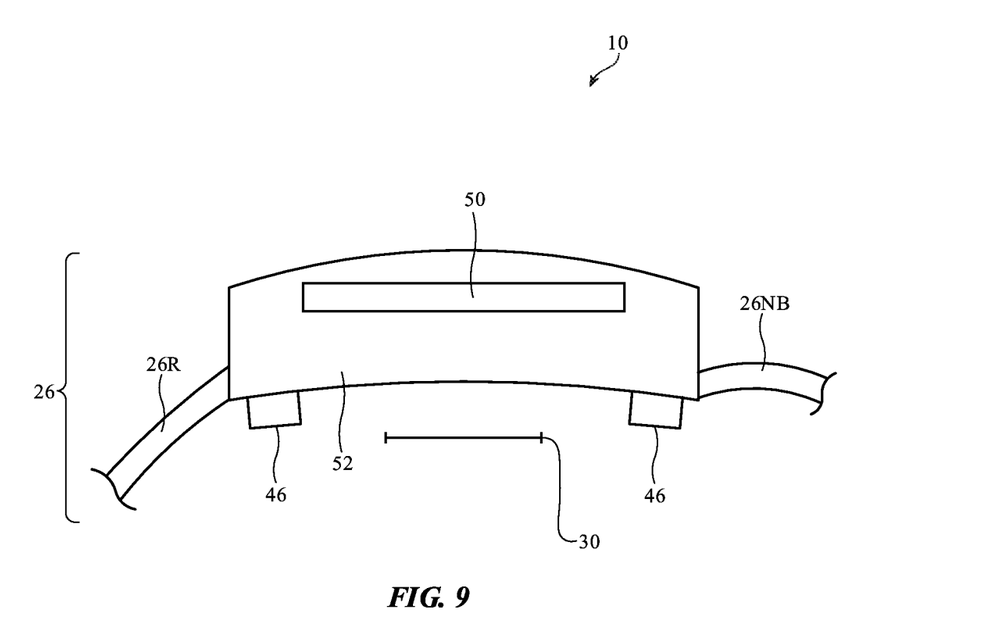
FIG. 9 is a top view of a portion of an illustrative head-mounted device such as a pair of goggles with individual eyecups and eye monitoring electrodes in accordance with an embodiment.

FIG. 9 is a top view of a left-hand portion of a pair of goggles having individual eye cups 52 joined by a flexible nose bridge portion such as portion 26NB. Portion 26NB may join left eye cup 52 of FIG. 9 (the portion of support structures 26 overlapping eye box 30) with a corresponding right eye cup. An optional optical component such as component 50 may be supported in each eye cup. Component 50 may be a display (e.g., display 14), an optical coupler (e.g., an optical coupler that allows real-world image light to pass through component 50 to eye box 30 and that helps direct an image from display 14 towards eye box 30), a lens such as a vision correction lens for a user, a clear glass or polymer lens (e.g., a lens for a pair of sunglasses), an optically opaque structure (e.g., so that device 10 of FIG. 9 may be used as a meditation device or a sleep mask device), and/or other optical components. Optional strap 26R may be configured to help secure device 10 on a user's head. Support structure 26 may be configured so that when device 10 is worn by a user, each eye cup rests against the user's face with inner rim 52 of the eye cup pressing electrodes 46 against the user's face so that electrooculography measurements may be made.

Figure 10:
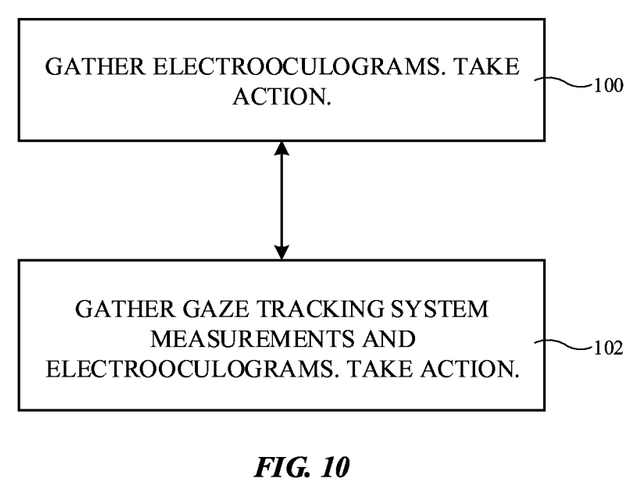
FIG. 10 is a diagram showing operations involved in using an electronic device with electrooculographic capabilities in accordance with an embodiment.

FIG. 10 is a diagram showing operations involved in using device 10. In the illustrative example of FIG. 10, device 10 has both an electrooculography sensor system for gathering electrooculograms and an image-sensor gaze tracking system (e.g., a gaze tracker having an image sensor, an infrared illumination system or other eye illumination system, etc.).

During the operations of block 100, device 10 may use the electrooculography sensor(s) in device 10 (e.g., electrodes 46 and associated signal measurement circuitry) to gather measurements on the user's eyes (e.g., electrooculograms). The electrooculogram data gathered during the operations of block 100 may reveal information on the direction of a user's gaze (eye orientation) and/or eye movements (changes in eye orientation). In some configurations, electrodes 46 may detect eye blinks and facial muscle movements associated with user facial expressions (e.g., so that this measured facial expression information may be used to animate an avatar associated with the user). In other configurations, eye movement information may be logged to provide information on a user's sleep cycles (e.g., when device 10 is a sleep mask or other device that may be used while the user's eyes are closed).

If desired, eye tracking from electrooculogram information may reveal information on where a user is gazing in the environment surrounding the user and device 10. Gaze information may be used as user input (e.g., a user may select an option displayed by display 14 by dwelling the user's gaze on that displayed option for more than a predetermined time and/or the user's gaze may be used as pointing input that is combined with a voice command or other input to select an option).

Information on the current focus of a user's visual attention may be used by device 10 to provide context that device 10 uses in providing output to a user. If, as an example, a user is traveling along a street and is viewing a particular object, device 10 can use speakers, a display, haptic output devices, or other output devices to provide the user with information about the object (e.g., device 10 may provide the name of the object and other information about the object, may present selectable options associated with the object, etc. using visual output, audible output, and/or haptic output).

Device 10 can determine which objects are located in the vicinity of the user using an online database of objects (e.g., object identities and object locations) and/or using image recognition techniques. Device 10 can identify which object in the user's environment is being observed by the user using 1) information on the user's present geographic location gathered from a geographic location sensor such as a satellite navigation system sensor, 2) information on the orientation of device 10 relative to the environment from an orientation sensor such as an inertial measurement unit and/or other orientation sensor, and/or 3) information on the user's gaze (e.g. the direction in which the user's eyes are oriented relative to device 10). For example, device 10 can compare the user's direction of view (gaze direction gathered using the electrooculography system) to a map of the user's surroundings to determine which object is currently being viewed by the user. Information on an environmental object of interest (e.g., an object currently being viewed) may be retrieved wirelessly by device 10 from the on-line database and presented to the user. This information may include a visual label or other computer-generated content that is overlaid on the real-world image, an audible description, a visual or audio selectable option such as a selectable button presented by display 14 that a user may gaze at or otherwise select to direct device 10 to take further action.

In configurations in which device 10 contains only electrooculographic sensors and no supplemental gaze tracking systems (e.g., no gaze tracking systems based on image sensors, etc.), device 10 may continually perform the operations of block 100. In configurations in which device 10 contains an image-sensor-based gaze tracking system in addition to an electrooculography sensor system, operations may, upon satisfaction of appropriate mode transition criteria, transition to the operations of block 102 in which the gaze tracking system is activated. Any suitable conditions may be used to trigger transition between blocks 100 and 102. For example, because less power may be used in monitoring a user's eyes during block 100 (when only electrooculograms are gathered) than during the operations of block 102, device 10 may default to operation in block 100 whenever device 10 can operate satisfactorily without using the capabilities of an image sensor gaze tracking system. When one or more capabilities of the gaze tracking system are determined to be useful (e.g., when a user's eyes open so that the gaze tracking system can operate, when gaze tracking with enhanced angular accuracy and/or response time are desired, when biometric identification capabilities such as iris scanning and/or retinal scanning capabilities are desired, etc.), device 10 can transition to the operations of block 102.

During the operations of block 102, the gaze tracking system may replace the operations of the electrooculography sensor system and/or may supplement the operations of the electrooculography sensor system. Gaze tracking information may, for example, be used to gather user input, to determine where in a scene the user's visual attention is directed (e.g., to provide device 10 with context), may be used to supply a foveated display system with information on the user's direction of gaze, may be used to determine where to display computer-generated content on display 14 for viewing by a user, etc.).

As described above, one aspect of the present technology is the gathering and use of information such as information from input-output devices. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

Physical environment: A physical environment refers to a physical world that people can sense and/or interact with without aid of electronic systems. Physical environments, such as a physical park, include physical articles, such as physical trees, physical buildings, and physical people. People can directly sense and/or interact with the physical environment, such as through sight, touch, hearing, taste, and smell.

Computer-generated reality: in contrast, a computer-generated reality (CGR) environment refers to a wholly or partially simulated environment that people sense and/or interact with via an electronic system. In CGR, a subset of a person's physical motions, or representations thereof, are tracked, and, in response, one or more characteristics of one or more virtual objects simulated in the CGR environment are adjusted in a manner that comports with at least one law of physics. For example, a CGR system may detect a person's head turning and, in response, adjust graphical content and an acoustic field presented to the person in a manner similar to how such views and sounds would change in a physical environment. In some situations (e.g., for accessibility reasons), adjustments to characteristic(s) of virtual object(s) in a CGR environment may be made in response to representations of physical motions (e.g., vocal commands). A person may sense and/or interact with a CGR object using any one of their senses, including sight, sound, touch, taste, and smell. For example, a person may sense and/or interact with audio objects that create 3D or spatial audio environment that provides the perception of point audio sources in 3D space. In another example, audio objects may enable audio transparency, which selectively incorporates ambient sounds from the physical environment with or without computer-generated audio. In some CGR environments, a person may sense and/or interact only with audio objects. Examples of CGR include virtual reality and mixed reality.

Virtual reality: A virtual reality (VR) environment refers to a simulated environment that is designed to be based entirely on computer-generated sensory inputs for one or more senses. A VR environment comprises a plurality of virtual objects with which a person may sense and/or interact. For example, computer-generated imagery of trees, buildings, and avatars representing people are examples of virtual objects. A person may sense and/or interact with virtual objects in the VR environment through a simulation of the person's presence within the computer-generated environment, and/or through a simulation of a subset of the person's physical movements within the computer-generated environment.

Mixed reality: In contrast to a VR environment, which is designed to be based entirely on computer-generated sensory inputs, a mixed reality (MR) environment refers to a simulated environment that is designed to incorporate sensory inputs from the physical environment, or a representation thereof, in addition to including computer-generated sensory inputs (e.g., virtual objects). On a virtuality continuum, a mixed reality environment is anywhere between, but not including, a wholly physical environment at one end and virtual reality environment at the other end. In some MR environments, computer-generated sensory inputs may respond to changes in sensory inputs from the physical environment. Also, some electronic systems for presenting an MR environment may track location and/or orientation with respect to the physical environment to enable virtual objects to interact with real objects (that is, physical articles from the physical environment or representations thereof). For example, a system may account for movements so that a virtual tree appears stationery with respect to the physical ground. Examples of mixed realities include augmented reality and augmented virtuality. Augmented reality: an augmented reality (AR) environment refers to a simulated environment in which one or more virtual objects are superimposed over a physical environment, or a representation thereof. For example, an electronic system for presenting an AR environment may have a transparent or translucent display through which a person may directly view the physical environment. The system may be configured to present virtual objects on the transparent or translucent display, so that a person, using the system, perceives the virtual objects superimposed over the physical environment. Alternatively, a system may have an opaque display and one or more imaging sensors that capture images or video of the physical environment, which are representations of the physical environment. The system composites the images or video with virtual objects, and presents the composition on the opaque display. A person, using the system, indirectly views the physical environment by way of the images or video of the physical environment, and perceives the virtual objects superimposed over the physical environment. As used herein, a video of the physical environment shown on an opaque display is called "pass-through video," meaning a system uses one or more image sensor(s) to capture images of the physical environment, and uses those images in presenting the AR environment on the opaque display. Further alternatively, a system may have a projection system that projects virtual objects into the physical environment, for example, as a hologram or on a physical surface, so that a person, using the system, perceives the virtual objects superimposed over the physical environment. An augmented reality environment also refers to a simulated environment in which a representation of a physical environment is transformed by computer-generated sensory information. For example, in providing pass-through video, a system may transform one or more sensor images to impose a select perspective (e.g., viewpoint) different than the perspective captured by the imaging sensors. As another example, a representation of a physical environment may be transformed by graphically modifying (e.g., enlarging) portions thereof, such that the modified portion may be representative but not photorealistic versions of the originally captured images. As a further example, a representation of a physical environment may be transformed by graphically eliminating or obfuscating portions thereof. Augmented virtuality: an augmented virtuality (AV) environment refers to a simulated environment in which a virtual or computer generated environment incorporates one or more sensory inputs from the physical environment. The sensory inputs may be representations of one or more characteristics of the physical environment. For example, an AV park may have virtual trees and virtual buildings, but people with faces photorealistically reproduced from images taken of physical people. As another example, a virtual object may adopt a shape or color of a physical article imaged by one or more imaging sensors. As a further example, a virtual object may adopt shadows consistent with the position of the sun in the physical environment.

Hardware: there are many different types of electronic systems that enable a person to sense and/or interact with various CGR environments. Examples include head mounted systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mounted system may have one or more speaker(s) and an integrated opaque display. Alternatively, a head mounted system may be configured to accept an external opaque display (e.g., a smartphone). The head mounted system may incorporate one or more imaging sensors to capture images or video of the physical environment, and/or one or more microphones to capture audio of the physical environment. Rather than an opaque display, a head mounted system may have a transparent or translucent display. The transparent or translucent display may have a medium through which light representative of images is directed to a person's eyes. The display may utilize digital light projection, OLEDs, LEDs, μLEDs, liquid crystal on silicon, laser scanning light sources, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

The foregoing is merely illustrative and various modifications can be made to the described embodiments. The foregoing embodiments may be implemented individually or in any combination.

What is claimed is:

1. A head-mounted device, comprising:
   a head-mounted support structure;
   an electrooculography sensor configured to gather gaze information, wherein the electrooculography sensor comprises electrodes configured to measure electrooculograms containing the gaze information and eye blink and facial expression information;
an output device; and
control circuitry configured to:
   process the electrooculograms to separate the eye blink and facial expression information from the electrooculograms;
   identify a currently viewed object using the gaze information obtained from the processed electrooculograms; and
   use the output device to supply user output based on the currently viewed object.

2. The head-mounted device defined in claim 1 further comprising:
   a geographic location sensor configured to identify a current geographic location of the head-mounted support structure; and
   an orientation sensor configured to gather head-mounted support structure orientation information indicating a direction in which the head-mounted support structure is oriented, wherein the control circuitry is configured to identify the currently viewed object using the gaze information, the current geographic location, and the head-mounted support structure orientation information.

3. The head-mounted device defined in claim 2 wherein the output device comprises a display configured to supply a visual label for the currently viewed object.

4. The head-mounted device defined in claim 2 wherein the output device comprises a speaker configured to supply audio information on the currently viewed object.

5. The head-mounted device defined in claim 2 wherein the output device comprises a display configured to display a selectable visual option associated with the currently viewed object.

6. The head-mounted device defined in claim 2 wherein the geographic location sensor comprises a global positioning system sensor.

7. The head-mounted device defined in claim 2 wherein the orientation sensor comprises an inertial measurement unit.

8. The head-mounted device defined in claim 7 wherein the electrodes are configured to measure the electrooculograms when located adjacent to left and right eye boxes.

9. The head-mounted device defined in claim 1 further comprising a gaze tracking system with an image sensor that gathers image sensor gaze tracking system measurements.

10. The head-mounted device defined in claim 9 wherein the control circuitry is configured to transition between:
   a first mode of operation in which the gaze information from the electrooculography sensor is used in identifying the currently viewed object without using the image sensor gaze tracking system measurements; and
   a second mode of operation in which the image sensor gaze tracking system measurements are used in identifying eye orientation.

11. The head-mounted device defined in claim 1 wherein the head-mounted support structure comprises a pair of transparent lenses configured to overlap, respectively, left and right eye locations.

12. A head-mounted device, comprising:
   a head-mounted support structure;
   an electrooculography sensor that is supported by the head-mounted support structure and that is configured to gather an electrooculogram indicative of a gaze direction aligned with an object, wherein the electrooculography sensor comprises electrodes;
   a speaker configured to supply audio output based on the electrooculogram and based on information about the object; and
   control circuitry configured to use signals for the electrooculogram from the electrodes to identify activity selected from the group consisting of: eye blinks and facial expressions, wherein the control circuitry is configured to obtain the electrooculogram from the signals by separating the identified activity from the signals.

13. The head-mounted device defined in claim 12 further comprising a display configured to display content based on the electrooculogram.

14. The head-mounted device defined in claim 12 further comprising a global positioning system sensor configured to gather a geographic location information, wherein the speaker is configured to supply the audio output based on the electrooculogram and the geographic location information.

15. The head-mounted device defined in claim 12, wherein the signals contain electrooculogram information, eye blink information, and facial expression information.

16. A head-mounted device, comprising:
   a head-mounted support structure;
   an electrooculography sensor configured to gather gaze information, wherein the electrooculography sensor comprises electrodes configured to measure electrooculograms indicative of the gaze information using capacitive coupling to respective skin portions to measure the electrooculograms and wherein the electrodes are configured to not contact any skin to measure the electrooculograms;
   an output device; and
   control circuitry configured to:
      identify a currently viewed object using the gaze information; and
      use the output device to supply user output based on the currently viewed object.

* * * * *